United States Patent
Clark

(10) Patent No.: US 7,333,206 B2
(45) Date of Patent: Feb. 19, 2008

(54) LIGHT SCATTER MEASUREMENT APPARATUS AND METHOD

(75) Inventor: Roy Clark, Thousand Oaks, CA (US)

(73) Assignee: The Bowing Company, Chicago, IL (US)

( * ) Notice: Subject to any disclaimer, the term of this patent is extended or adjusted under 35 U.S.C. 154(b) by 292 days.

(21) Appl. No.: 11/100,780

(22) Filed: Apr. 7, 2005

(65) Prior Publication Data
US 2006/0227329 A1   Oct. 12, 2006

(51) Int. Cl.
*G01N 21/47* (2006.01)
(52) U.S. Cl. ............................. 356/446; 356/442
(58) Field of Classification Search ........ 356/436–446; 250/343
See application file for complete search history.

(56) References Cited

U.S. PATENT DOCUMENTS

| | | | |
|---|---|---|---|
| 6,233,052 B1 * | 5/2001 | Zare et al. ................ | 356/437 |
| 6,392,753 B1 | 5/2002 | Logunov | |
| 6,466,322 B1 | 10/2002 | Paldus et al. | |
| 6,480,282 B1 * | 11/2002 | Chinowsky et al. ........ | 356/445 |
| 6,490,039 B2 | 12/2002 | Maleki et al. | |
| 6,515,749 B2 | 2/2003 | Pipino | |
| 6,609,068 B2 | 8/2003 | Cranley et al. | |
| 6,694,067 B1 | 2/2004 | O'Keefe et al. | |
| 6,727,492 B1 | 4/2004 | Ye et al. | |

OTHER PUBLICATIONS

An, K.; C. Yang, R.R. Dasari & M.S. Feld, Optics letts. 20(9) 1068-1070 (1995), Cavity ringdown technique and its application to the measurement of ultraslow velocities.

Anderson, D.Z., J.C, Frisch & C.S. Masser, Applied Optics 23(8) 1238-1245 (1984), Mirror reflectometer based on cavity decay time.

Billardon, M. , et al., Applied Optics 30(3) 344-351 (1991), Fabry Perot effects in the exponential decay and phase shift reflectivity measurement methods.

Clark, R., Optical Engineering 32(3) 571-584 (1993), Optical measurement with direct traceability to the primary standards of length and time: toward a system of metrology bas.

Fabre, C.; R.G. Devoe & R.G. Brewer, Optics Letters 11(6) 365-7 (1986), Ultrahigh finesse optical cavities.

Fox, R.W. & L. Hollberg, Optics Letters 27(20) 1833-1835 (2002), Role of spurious reflections in ringdown spectroscopy.

(Continued)

*Primary Examiner*—Gregory J. Toatley, Jr.
*Assistant Examiner*—Tri Ton
(74) *Attorney, Agent, or Firm*—MacPherson Kwok Cher & Heid LLP; Clifford G. Cousins

(57) ABSTRACT

In accordance with an embodiment of the present invention, an apparatus for measuring light scatter loss from a test piece includes a light source, an optical cavity including the test piece and at least one mirror located along a path, and a light detector. The cavity receives an input beam from the light source, circulates a beam within the cavity as a circulating beam, and produces an output beam. Irregularities on the surface of the test piece result in a progressive diffusion of the circulating beam about the path. The light detector provides an output signal based on the intensity of the output beam. The output signal has an initial slope that determines a first saturation value. The output signal has a second saturation value. The difference between the first saturation value and the second saturation value provides a scatter loss measurement.

24 Claims, 11 Drawing Sheets

OTHER PUBLICATIONS

Fidric, B.G.; R.A. Provencal, S.M. Tan, E.R. Crosson, A.A. Kachanov & B.A. Paldus, OPN 14(7) 24-29 (2003), Bananas, Explosives and the future of Cavity Ringdown Spectros.

Gupta, M.; H. Jiao & A. O'Keefe, Optics Letts 27(21) 1878-1880 (2002), Cavity enhanced spectroscopy in optical fibers.

Herbelin, J.M., et al., Applied Optics 19(1) 144-147 (1980), Sensitive measurement of photon lifetime and true reflectances in an optical cavity by a phase-shift method.

Kim, J.W., et al., Applied Optics 40(30) 5509-5516 (2001), Uncertainty analysis of absolute concentration measurement with continuous-wave cavity ringdown spectroscopy.

Kwok, M. A. & R.H. Ueunten, Optical Engineering 23(6) 776-779 (1984), Determining hydrogen fluoride mirror reflectances with the cavity phse shift method.

Lee, J.Y., et al. Applied Optics 39(12) 1941-1945 (2000), Measurement of ultralow supermirror birefringence by use of the polarimetric diferential cavity ringdown technique.

Leeuwen, N.J. Van, J.C. Diettrich & A.C. Wilson, Applied Optics 42 (18) 3670-3677 (2003), Periodically locked cw cavity ringdown spectroscopy.

Lerber, T.V. et al., Applied Optics 41(18) 3567-3575 (2002), Cavity ring down principle for fiber optic resonators: experimental realization of bending loss and evanescent . . . .

Li, D., D. Coyne et al., Applied Optics 38(25) 5378-5383 (1999), Optical contamination screeing of materials with a high finesse Fabry-perot cavity resonated continuously at.

Logunov, S.L., Applied Optics 40(9) 1570-1573 (2001), Cavity ringdown detection of losses in thin films in the telecommunication wavelength window.

Naus, H. et al., Applied Optics 40(24) 4416-4426 (2001), Quantitative analysis of decay transients applied to a multimode pulsed cavity ringdown experiment.

O'Keefe, A. & D.A.G. Deacon, Rev. Sci. Instruments 59 2544-2551 (1988), Cavity ringdown optical spectrometer measurements using pulsed laser sources.

Paldus, B.A., et al., Optics Letts 25(9) 666-669 (2000), Cavity ringdown spectroscopy using mid-infrared quantum-cascade lasers.

Paul, J.B., et al., Applied Optics 40(27) 4904-4910 (2001), Ultrasensitive absorption spectroscopy with a high finesse optical cavity and off axis alignment.

Scherer, J.J., J.B. Paul, H. Jiao & A. O'Keefe, Applied Optics 40(36) 6725-6732 (2001), Broadband ringdown spectral photography.

Totschnig, G., D.S. Baer, J. Wang, F. Winter, H. Hofbauer & R.K. Hanson, Applied Optics 39(12) 2009-2016 (200), Multiplexed continuous wave diode laser cavity ringdown meas.

Uehara, N., A. Ueda, K. Ueda, H. Sekiguchi, T. Mitake, K. Nakamura Optics Letts. 20(6) 530-532 (1995), Ultralow loss mirror of the parts in 106 lev.

Wang, G.,et al., Applied Spectroscopy 56(3) 386-397 (2002), Cavity ringdown spectroscopy for diagnostic and analytical measurements in an inductively coupled plasma.

Barmenkov, Yu O., A. Ortigosa-Blanch, A. Diez, J. L. Cruz & M. V. Andres, Optics Letters 29(21) 2461-2463 (2004), Time domain fiber laser hydrogen sensor.

Von Basum, G.et al., Optics Letters 29(8) 797-799 (2004), Parts per trillion sensitivity for ethane in air with an optical parmetric oscillator cavity leak out spectrometer.

Hahn J. W, et al., Applied Optics 38(9) 1859-1866 (1999), Cavity ringdown spectroscopy with a cw laser: calculation of coupling efficiency and a new spectrometer design.

Jacob D.; F. et al., Applied Optics 33(15) 3175-3178 (1994), Pulsed measurement of high reflectivity mirror phase retardances.

Taylor, Howard M., Chapter VIII Brownian Motion and Related Processes, (1998), pp. 473-541, An introduction to stochastic Modeling.

Levensen M. D., et al.,Optics Letters 25(12) 920-923 (2000), Frequency switched heterodyne cavity ringdown spectroscopy.

Marcus G. A. & H. A. Schwettman, Applied Optics 41(24) 5167-5171 (2002), Cavity ringdown spectroscopy of thin films in the mid IR.

Moore C.: S. P. Chan J. N. Demas & B. A. Degraff, Applied Spectroscopy 58(5) 603-607 (2004), Comparison of methods for rapid evaluation of lifetimes of exponential decays.

Naik S. V., et al., Applied Optics 43(26) 5116-5125 (2004), Measurements of absolute CH concentrations by cavity ring down spectroscopy and linear . . . .

Pipino A. C. R., Applied Optics 39(9) 1449-1453 (2000), Monolithic folded resonator for evanescent wave cavity ringdown spectroscopy.

Rempe G.: R. J. Thompson H. J. Kimble & R. Lalezari, Optics Letters 17(5) 363-365 (1992), Measurement of ultralow losses in an optical interferometer.

Sneep M.; S. Hannermann E. J. Van Duijn & W. Ubachs, Optics Letters 29(12) 1378-1380 (2004), Deep UV cavity ringdown spectroscopy.

Stewart G.; K. Atherton & B. Culshaw, Optics Letters 29(5) 442-444 (2004), Cavity enhanced spectroscopy in fiber cavities.

Tarsa P. B.; D. M. Brzozowski, P. Rabinowitz & K. K. Lehman, Optics Letters 29(12) 1339-1341 (2004), Cavity ringdown strain gauge.

Vaschenko, G., et al., Applied Optics 42(22) 4584-4589 (2003), Characterization of thin film losses with a synchronously pumped ringdown cavity.

Vogler D. E.; M. G. Muller & M. W. Sigrist, Applied Optics 42(27) 5413-5416 (2003), Fiber optic cavity sensing of hydrogen diffusion.

Wang C., et al., Applied Spectroscopy 58(6) 734-740 (2004), Measurement of OH radicals in a low power atmospheric inductively coupled plasma by cavity ringdown spectroscopy.

Wang, C. & S. T. Scherrer, Optics Letters 29(4) 352-354 (2004), Fiber ringdown pressure sensors.

Wang C. & S. T. Scherrer, Applied Optics 43(35) 6458-6464 (2004), Fiber loop ringdown for physical sensor development: pressure sensor.

Wang C., et al., Applied Spectroscopy 58(7) 784-791 (2004), Measurement of cavity ringdown spectroscopy of acetone in the UV and NIR spectral regions: potential for . . . .

Williams S., et al., Optics Letters 29(10) 1066-1068 (2004), Quantitative detection of singlet O2 by cavity enhanced absorption.

Yang W.; A. Joshi & M. Xiao Optics Letters 29(18)2133-2135 (2004), Enhancement of the cavity ringdown effect based on electromagnetically induced transparency.

\* cited by examiner

LIGHT SCATTER MEASUREMENT APPARATUS AND METHOD

TECHNICAL FIELD

The present invention relates generally to optical characterization, and more particularly to determining the scatter loss from a surface.

RELATED ART

The characterization of an optical surface, such as a high performance optical dielectric coating, can include the determination of losses due to reflection, transmission, absorption, and light scatter. As the reflectivity or transmission increase, conventional light intensity based measurements become less accurate and other methods are used instead. One alternative method, utilizes a passive cavity decay time property known as a cavity ringdown technique. In this method, a coated test piece or test article is introduced into a passive optical resonant cavity where the observed change in cavity decay time is related to the additional losses induced by the test article coating. This technique only provides a measure of the total cavity losses which include, for a highly reflective coating, absorption, transmission and light scatter. Since the effects of these properties are combined, additional measurements are needed to determine the individual loss contributions due to absorption, transmission and scatter.

The ringdown measurement of mirror reflectivities yields a cavity loss that includes both mirror transmission and absorption. In order to separate these two parameters, at least one of them has to be independently measured. One technique for separating these parameters is to measure the mirror heating directly when it is illuminated by a suitable light source, such as a laser beam. The temperature rise related to the coating absorption can be measured directly using an infrared (IR) camera. However, measurement errors inherent with this technique can be significant. An alternative technique includes measuring a change in a beat frequency between two adjacent modes in a stabilized resonant cavity where the change in beat frequency is as a function of the laser power. The frequency shift manifested as the change in beat frequency can be related to a thermally induced distortion on a cavity mirror surface caused by absorption.

Thus, there remains a need for an apparatus and method to measure the effects of scatter losses isolated from the absorption and transmission losses of an optical system.

SUMMARY

Apparatuses and methods are disclosed herein to provide for measurement of scatter losses. For example, in accordance with an embodiment of the present invention, an apparatus for measuring light scatter loss from a test piece includes a light source, an optical cavity including the test piece and at least one mirror located along a path, and a light detector. The cavity receives an input beam from the light source, circulates a beam within the cavity as a circulating beam, and produces an output beam. The circulating beam undergoes a progressive diffusion of the circulating beam about the path. The light detector provides an output signal based on the intensity of the output beam. The output signal has an initial slope that determines a first saturation value. The output signal also has a second saturation value. The difference between the first saturation value and the second saturation value provides a scatter loss measurement.

According to another embodiment of the present invention, an apparatus for measuring light scatter loss from a test piece includes a light source, an optical cavity including the test piece and at least one mirror located along a path, a light detector, and a computer. The light source provides an input beam. The optical cavity includes the test piece and at least one mirror located along a path. The cavity is configured to receive the input beam, to circulate a beam within the cavity as a circulating beam, and to produce an output beam. Irregularities on the surface of the test piece result in a progressive diffusion of the circulating beam about the path. The light detector provides an output signal based on the intensity of the output beam. The computer receives a representation of the output signal and calculates a slope. The computer calculates a first saturation value from the slope, and stores a second saturation value. The computer calculates the difference between the first saturation value and the second saturation value to provide a scatter loss measurement.

According to yet another embodiment of the present invention, a method of measuring light scatter loss from a test piece includes applying light to an optical cavity including the test piece and at least one mirror producing a circulating beam within the cavity and an output beam from the cavity. The method further includes detecting a first intensity value from the output beam at a first time to determine a first coordinate, detecting a second intensity value from the output beam at a second time to determine a second coordinate, and detecting a scattered intensity saturation value at a third time. The method further includes computing an unscattered intensity saturation value from a predicted unscattered intensity saturation curve having a corresponding curve portion that matches the slope of a line through the first coordinate and the second coordinate, and computing the difference between the unscattered intensity saturation value and the scattered intensity saturation value to provide a scatter loss measurement.

The present invention fulfills a long felt need in the industry, for characterizing high performance optical components in particular, that could become an industry standard related to the characterization of optical elements used in diverse technology areas including lasers, telescopes, and medical instrumentation.

The scope of the invention is defined by the claims, which are incorporated into this section by reference. A more complete understanding of embodiments of the present invention will be afforded to those skilled in the art, as well as a realization of additional advantages thereof, by a consideration of the following detailed description. Reference will be made to the appended sheets of drawings that will first be described briefly.

BRIEF DESCRIPTION OF THE DRAWINGS

Embodiments of the present invention and their advantages are best understood by referring to the detailed description that follows. It should be appreciated that like reference numerals are used to identify like elements illustrated in one or more of the figures.

DETAILED DESCRIPTION

Figure 1:
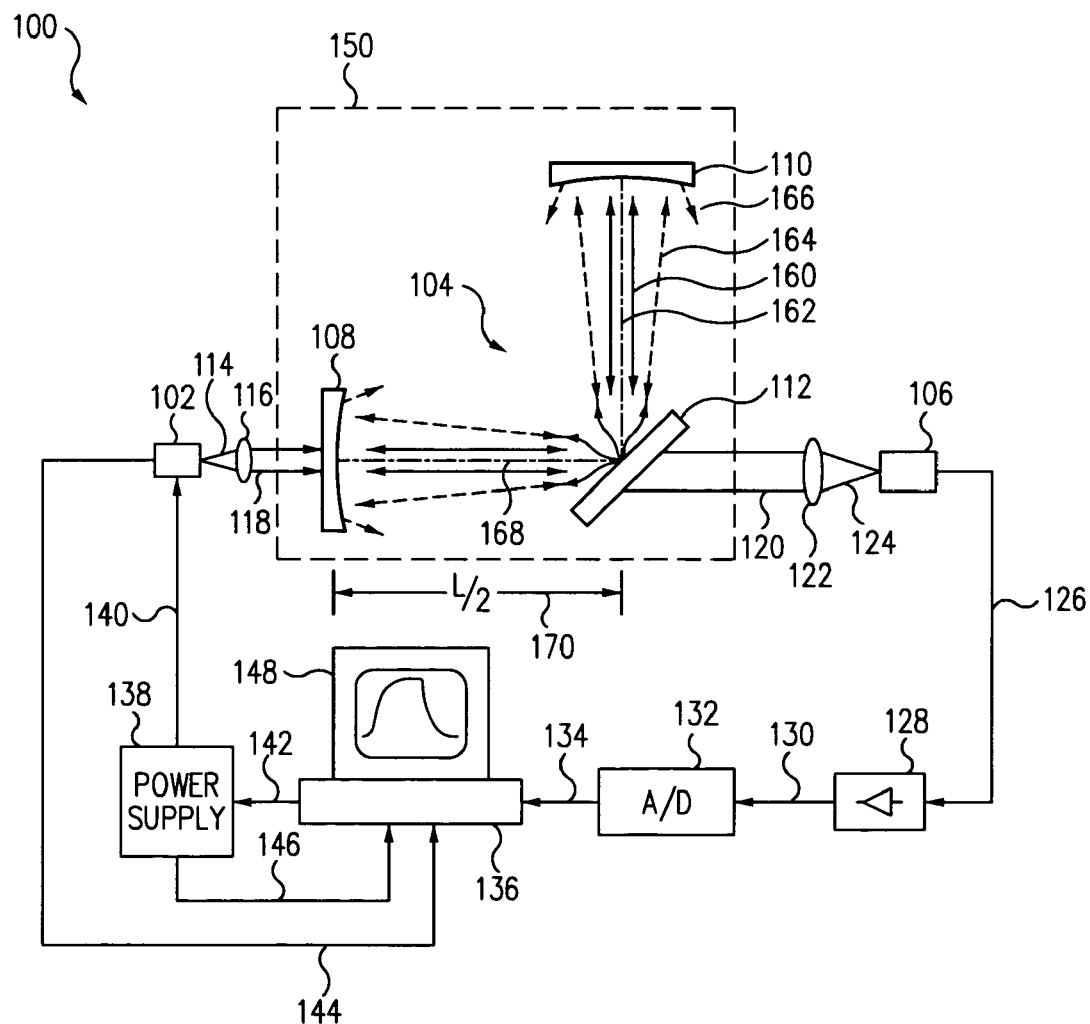
FIG. 1 shows an optical scatter measurement apparatus in accordance with an embodiment of the present invention.

In reference to FIG. 1, an optical scatter measurement system 100 includes a light source 102, a passive optical cavity 104, and a detector 106. Light source 102 provides a light beam to excite the cavity 104. In this embodiment, the cavity 104 includes a first end mirror 108, a second end mirror 110, and a test piece 112 configured to form an L-shaped arrangement where the end mirrors form the legs of cavity 104 and are located symmetrically about the test piece.

In this embodiment, the legs are spaced at 90-degrees so that test piece 112 is located at about 45-degrees having a normal that bisects the angular distance between the two legs of cavity 104. End mirrors (108, 110) each have a planar surface and a highly reflective concave surface. The test piece 112 has a reflective planar surface facing the cavity and can be set at a 45-degree angle to form the L-shaped cavity 104 where the concave surface of the first end mirror 108 is oriented towards the planar surface of the test piece, and the concave surface of the second end mirror 110 is also oriented towards the planar surface of the test piece 112. In this manner, cavity 104 is formed where light within the cavity is circulated between the end mirrors (108, 110) and reflected off the surface of test piece 112.

Light source 102 provides a light beam 114 that can be collimated, if necessary, by a first lens 116 to provide a collimated input beam 118 for application to cavity 104. In the case where light beam 114 is already collimated, light beam 114 is input beam 118 from light source 102 and is used to illuminate or excite cavity 104. Light source 102 can be a laser providing an output beam at wavelength(s) suitable for characterizing the test piece at the desired wavelength design point(s). Suitable wavelengths include ultra-violet (UV), visible (Vis), near infra-red (NIR), and infra-red (IR) regions of the electromagnetic spectrum. Similarly, an output beam 120, comprising light exiting cavity 104 that is reflected from first end mirror 108 and transmitted through test piece 112, can be focused by a lens 122, if necessary, to become a converging output beam 124 that is applied to detector 106. In the case where focusing of output beam 120 is not needed, output beam 120 is applied directly to detector 106.

Detector 106 receives output beam 120 and produces an analog, or continuous, output signal 126 that is amplified, if necessary, by an amplifier 128 to produce an amplified analog output signal 130. In this manner, amplified analog output signal 130 is a representation of analog output signal 126. Detector 106 includes a photosensitive device, or transducer, such as a photodiode, capable of converting the light energy from output beam 120 into a signal corresponding to the intensity of the received light energy. Any suitable detector that can operate at the desired wavelength and with the desired frequency response can be used. For UV, Vis and short NIR wavelengths, silicon photodiodes or photomultipliers may be used. For NIR and IR wavelengths various detectors are available, each with its own wavelength range and frequency response. Suitable detectors may include Germanium (Ge), Gallium Arsenide (GaAs), Indium Phosphide (InP), Gallium Indium Phosphide (GaInP), Indium Antimonide (InSb) and mercury Cadmium Telluride (HgCdTe).

Amplified detector output signal 130 is then converted from analog to digital form by an analog to digital converter 132, or digitizer, into a digital output signal 134 which is then captured, stored and analyzed by a data acquisition system 136, also known as a suitably programmed computer, microprocessor, microcontroller, or processor. Light source 102 is driven by a power supply 138 through a power signal 140 applied to light source 102. Power signal 140 controls the activation, deactivation, and illumination power output of light source 102. Power supply 138 is activated by a power supply control signal 142 from computer 136. A first synchronization signal 144 from light source 102 can be used to synchronize with data acquisition system 136. Alternatively, a second synchronization signal 146 from power supply 138 can be used to synchronize with data acquisition system 136. If power supply 138 is self-pulsing, it is preferable to use synchronization signal 146 to control sampling of detector output signal 126 and including system latencies. A display monitor 148 can display a graphical representation of the intensity of light within cavity 104 as a function of time. Display monitor 148 provides a visual representation of the time varying detected signal 126 and can be a cathode ray tube (CRT) or an oscilloscope, for example. An enclosure 150 may be used to isolate cavity 104 from environmental factors, such as atmospheric water vapor, contaminants, or to act as a container for a preferred environment such as nitrogen gas. When enclosure 150 is used, windows are provided to permit input beam 118 and output beam 120 to traverse the boundary of enclosure 150.

According to an embodiment of the present invention, an apparatus and method are provided for separately determining scatter losses by inducing and measuring two different rise or decay times within a resonant cavity in order to distinguish between losses due to both the combined absorption and transmission alone and losses due to the combined effects of absorption, transmission, and scatter. These rise or decay times are measured during two different measurement periods. During a first measurement period, when the cross sectional size of the light beam used to excite the cavity is much smaller than the cross sectional size of the cavity mirrors, there is a transient period when the light is still filling cavity 104. During this time, the only losses are due to absorption and reflection. During a second measurement period, after the light has filled cavity 104 and begun to spill over outside the confines of cavity 104, scatter losses change the temporal behavior of cavity 104 exhibiting behavior based on the absorption, transmission and scatter loss together, allowing the combined effects to be determined. Since the second measurement period includes a unique term, the scatter loss, the difference between the first measurement and the second measurement will yield a measurement of the scatter loss. When test piece 112 includes a high performance dielectric coating, the scatter loss measurement can be used to characterize the dielectric coating. In cases where such coatings are designed to operate at two or more wavelengths or wavelength ranges, characterization at more than one wavelength may be needed to completely characterize the coating. When light source 102 is first activated, the circulating beam 160 in cavity 104 is collimated and is close to an optical axis 162 which is the center of a portion of an optical path within cavity 104. In this manner, the area of the circulating beam 160 cross section is much smaller than the area of the end mirrors (108, 110) that form the cavity. A typical value may be greater than about 100:1 for the ratio of the area of an end mirror (108, 110) to the circulating beam 160 cross sectional area.

Irregularities on the surface of test piece 112 cause a progressive diffusion of the circulating beam where circulating beam 164 progressively spreads about optical axis 162. This diffusion increases as the optical power begins to build in the cavity and the residence time increases. As the residence time increases, the intensity reaches steady state and the intensity gain due to cavity 104 is balanced by the combined scatter, absorption and transmission losses. As the scatter induced diffusion continues to increase with time, part of the circulating beam 166 is lost due to divergent or diffusive reflections that remove light from cavity 104. The scatter loss reduces the accumulation of optical power in cavity 104 compared to the case of just absorption and transmission.

During the first measurement period, while light in cavity 104 is not lost due to scatter, the amount of light energy within cavity 104 continues to build. In order to analyze and extract the scatter loss from the time dependence of the cavity rise time, a mathematical model is herein proposed. Let one unit of light intensity accumulate in the cavity during each round trip circulation. The round trip path requires one reflection at each curved end mirror (108, 110) and two reflections at test piece 112 so that an optical ray returns to the same plane perpendicular to the optical axis of the cavity from which it started. The corresponding round trip time of the circulating beam, t, is given by:

$$t = 2L/c \qquad \text{(Equation-1)}$$

where L is the cavity length and c is the velocity of light in the cavity. During this round trip, some light is lost at each of the mirrors due to absorption and transmission at the mirrors, while one unit of light intensity is added. The light intensity at the end of one round trip or circulation through cavity 104 is given by:

$$It = 1 + [It-1] \times R \qquad \text{(Equation-2)}$$

where It-1 is the start intensity, R is the product of the mirror reflectivities:

$$R = R1 \times R2 \times R3 \times R2 \qquad \text{(Equation-3)}$$

where R1 and R3 represent the reflectivities of the curved end mirrors (108, 110), and R2 represents the reflectivity of test piece 112. For various embodiments including a different number of mirrors, the product of the mirror reflectivities will correspond to the number, type, and quality of optical elements forming cavity 104.

In one example, the reflectivity of end mirrors (108, 110) is 0.9998 each and the reflectivity of test piece 112 is 0.9995. During the period when all the light in circulating beam 160 is contained within cavity 104, and none of the light in cavity 104 is lost due to scatter, the intensity losses in cavity 104 are due entirely to absorption and transmission within cavity 104, while additional losses once light escapes cavity 104 are due to scatter from test piece 112. In this example, losses due to scatter vary from 200 to 2000-ppm. For this example, end mirrors (108, 110) have a radius of curvature of 600-cm and the cavity length L is 50-cm, with the length of both legs equal to 25-cm. This gives a round trip time of 0.00333 microseconds.

The circulating beam cross section diameter is initially 0.2 cm while both end mirror (108, 110) diameters are 2.54 cm. This configuration provides an area ratio of approximately 160:1 for the mirror diameter to the circulating beam cross section diameter during the first measurement period. A ratio of at least about 100:1 is preferable. In this embodiment, the distance between first end mirror 108 and test piece 112 along a central axis 168 is L/2 170, and the distance between second end mirror 110 and test piece 112 is L/2 172 along central axis 162, comprising a total distance L. Central axis 162 and central axis 168 together comprise the central path of cavity 104 since this is the path of the circulating beam 160. Although both legs may be equal in length, such a limitation is not necessary. Detector 106 is aligned with central axis 168 so as to receive light reflected from first end mirror 108 and transmitted through test piece 112.

Figure 2:
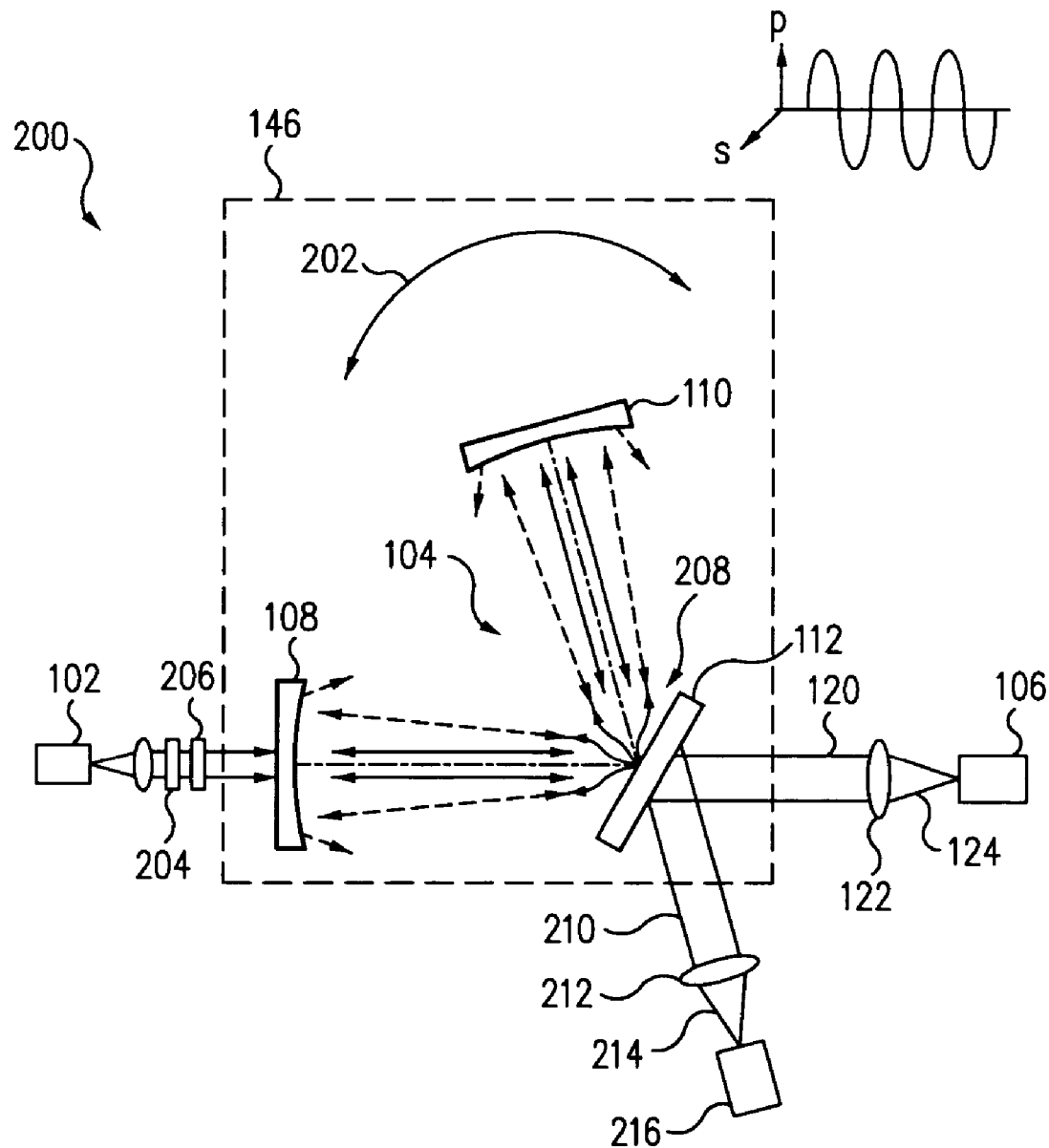
FIG. 2 shows an optical cavity apparatus where a second end mirror can be moved to a different angular position in accordance with an embodiment of the present invention.

FIG. 2 shows an optical cavity apparatus 200 where second end mirror 110 can be moved to a different angular position 202 relative to test piece 112 while maintaining the path (162, 168) of cavity 104. Correspondingly, the angle test piece 112 makes with both first end mirror 108 and second end mirror 110 is equal so that test piece 112 is located symmetrically between the end mirrors (108, 110) for enabling light to be circulated within cavity 104 as a circulating beam. This permits coating performance to be evaluated over a wide range of angles of incidence, since coating performance may be specified at one or more angles. In one alternative, detector 106 can be aligned with central axis 162 so as to receive light reflected from second end mirror 110 and transmitted through test piece 112.

Coating performance, for either reflective or transmissive optics may also be specified for a given polarization of the incident light. Typically, polarization is defined in terms of s and p linear polarization as shown with reference to FIG. 2. The electric vector of p-polarized light oscillates in the plane of the figure whereas for s-polarized light the electric vector oscillates perpendicular to the plane of the figure. Polarizing element 204 is a linear polarizer, which converts beam 118 into a linearly polarized beam of light. Polarizing element 206 is an optical retarder, which may variously rotate the plane of linearly polarized light, or convert linearly polarized light into elliptical or circularly polarized light.

Polarizing elements 204 and 206 may be incorporated singly or in combination into the collimated input beam 118 to control the polarization of the incident beam. Test piece 112 may include a coating layer 208 such as a high performance optical coating for use on lenses. Test piece 112 can be included with one or more optical elements, such as lenses, during a coating operation so that test piece 112 receives the same coating as the optical elements. Test piece 112 may then be examined to characterize the applied coating while direct examination of the coated lenses may be impractical or undesirable.

A second output beam 210, comprising light exiting cavity 104 that is reflected from second end mirror 110 and transmitted through test piece 112, can be focused by a lens 212, if necessary, to become a converging output beam 214 that is applied to a detector 216. In the case where focusing of output beam 210 is not needed, output beam 210 is applied directly to detector 216. Either detector 106 or detector 216 may be used singly or in combination.

Figure 3:
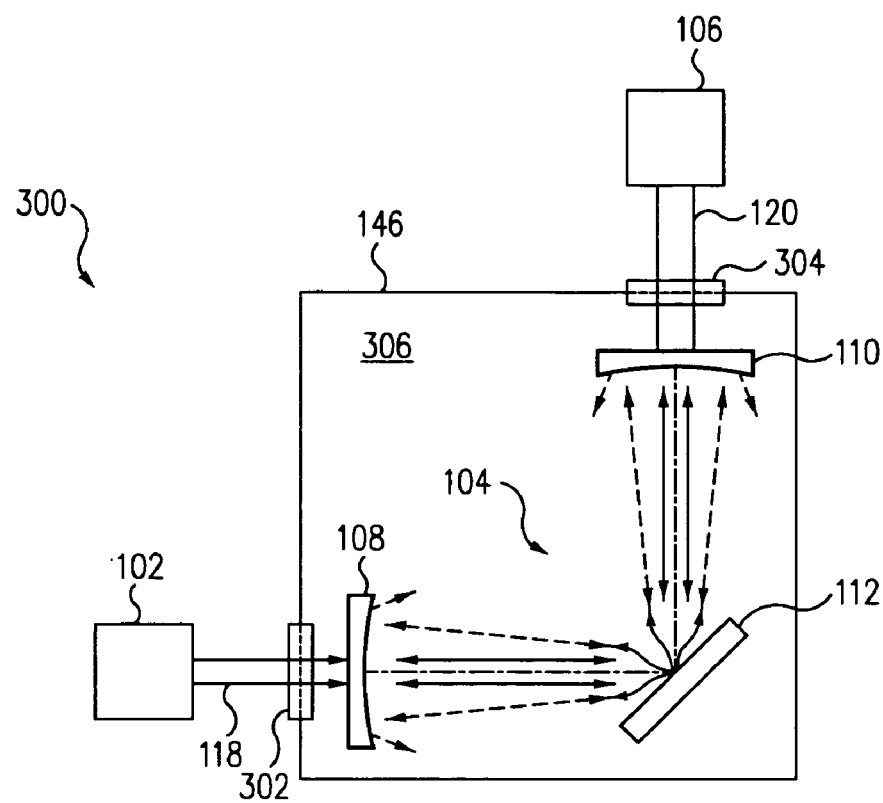
FIG. 3 shows an optical cavity apparatus where the output beam detector is positioned to receive the output beam adjacent to the second end mirror in accordance with an embodiment of the present invention.

FIG. 3 shows an optical cavity apparatus 300 where output beam detector 106 is located in a position to receive output beam 120 adjacent to second end mirror 110. In this configuration, the scatter loss from the surface of an opaque test piece 112 may be characterized since light does not pass through opaque test piece 112. FIG. 3 also shows enclosure 150 for isolating cavity 104 or for providing a controlled environment surrounding cavity 104. Enclosure 150 includes a first window 302 for transmitting input beam 118 into enclosure 134 and window 304 for transmitting output beam 120 out of enclosure 134. An interior region 306 of enclosure 134 can be evacuated or alternatively may contain a known type or mixture of gas so that the scatter measurement may be performed largely without environmental interferences, or within a controlled environment.

Figure 4:
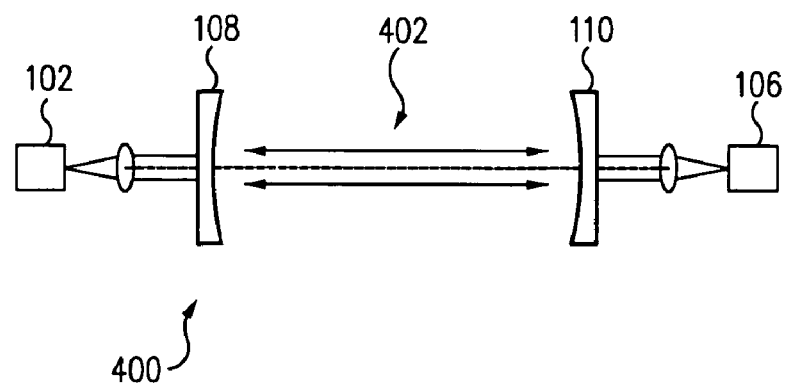
FIG. 4 shows an optical cavity apparatus used for determining the scatter losses due to just the two curved end mirrors in accordance with an embodiment of the present invention.

FIG. 4 shows an optical cavity apparatus 400 wherein the losses due to just the two curved end mirrors (108, 110) in a cavity 402 may be determined. In a strictly literal sense, all surfaces have some degree of irregularity and can contribute to scatter. For convenience, it may be assumed that there is no scatter contribution from end mirrors (108, 110). However, for higher accuracy, the scatter due to end mirrors (108, 110) may be determined using the configuration of FIG. 4, and then subtracted from the scatter term determined for test piece 112. Alternatively, the scatter losses due to a highly tranmissive optical element may be determined by inserting the element into cavity 402, approximately midway between first end mirror 108 and second end mirror 110, so that light circulating within the cavity passes through the element.

Figure 5:
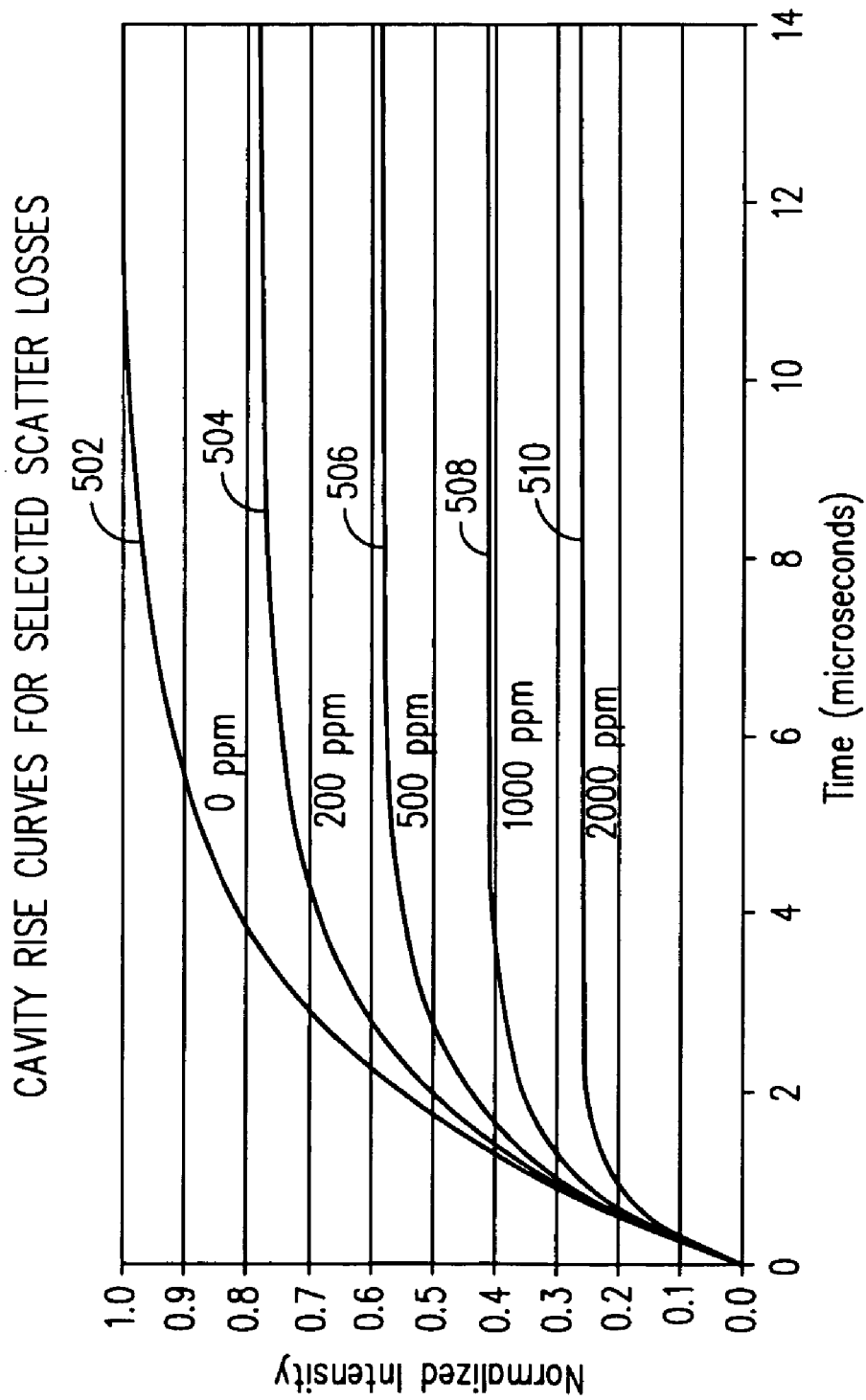
FIG. 5 shows a collection of cavity rise curves having different scatter losses and showing the normalized intensity over time where the saturation value of a predicted 0-ppm scatter curve is used for normalization in accordance with an embodiment of the present invention.

FIG. 5 shows a collection of cavity 104 rise curves having different scatter losses and showing the normalized intensity over time where the saturation value of a predicted 0-ppm scatter curve 502 is used for normalization. The cavity rise curves show the intensity within cavity 104 based on the output of detector 106 as described above. The assumption that the cavity loss due to scatter has the same time dependence function as the losses due to transmission and absorption is not strictly true. This aspect was examined using a nonsequential geometric ray tracing program, Light Tools, to simulate the intensity rise curves of the resonant cavity as shown in FIG. 5. In this example, for a test piece with irregularities that correspond to a measurement of 200-ppm, cavity 104 saturates as shown in curve 504 by saturating at approximately 77.9% of the 0-ppm curve 502 maximum saturation value.

Similarly, for a test piece with irregularities that correspond to a measurement of 500-ppm, cavity 104 saturates at approximately 58.4% of the 0-ppm curve 502 saturation value as shown in a curve 506. For test piece with irregularities that correspond to a measurement of 1000-ppm, cavity 104 saturates at approximately 41.3% of the 0-ppm curve 502 saturation value as shown in curve 508. Finally, a test piece with irregularities that correspond to a measurement of 2000-ppm, a curve 510 causes cavity 104 to saturate at approximately 26.0% of the 0-ppm curve 502 saturation value.

The cavity intensity rise time for each curve can be calculated iteratively using Equation-2 with R2 set to [0.9995-Sppm/(10^6)], where Sppm is the scatter term (S) in parts-per-million. A technique for determining the scatter loss term includes determining the initial slope of the measured curve and predicting the 0-ppm scatter loss curve. In the first period, up to about 1 microsecond in this example, the slopes of all curves (502-510) are essentially the same, and correspond to where circulating beam 160 is filling cavity 104 and the only losses are due to the combined absorption and transmission losses. The time of the first period is determined by the behavior of the saturation curves (502-510) and can differ from these examples due to changes in light source 102 and the relevant technology such as a different wavelength of light from light source 102.

In an actual measurement, only a curve including scatter would be measured. However, the initial slope allows the upper curve to be predicted or calculated. More specifically, the saturation value of the predicted 0-ppm scatter case may be determined based on the slope of the detected intensity during the period when light is still filling the cavity and the only losses are due to transmission and absorption. All of the intensity curves will saturate over time since there are unavoidable losses within the optical apparatus including transmission losses and the power output of light source 102 is finite, or not usable beyond a known power output level. The difference between the two curves after reaching saturation allows the scatter loss to be determined. In this example, saturation occurs at long time scales greater than about 12 microseconds.

Figure 6:
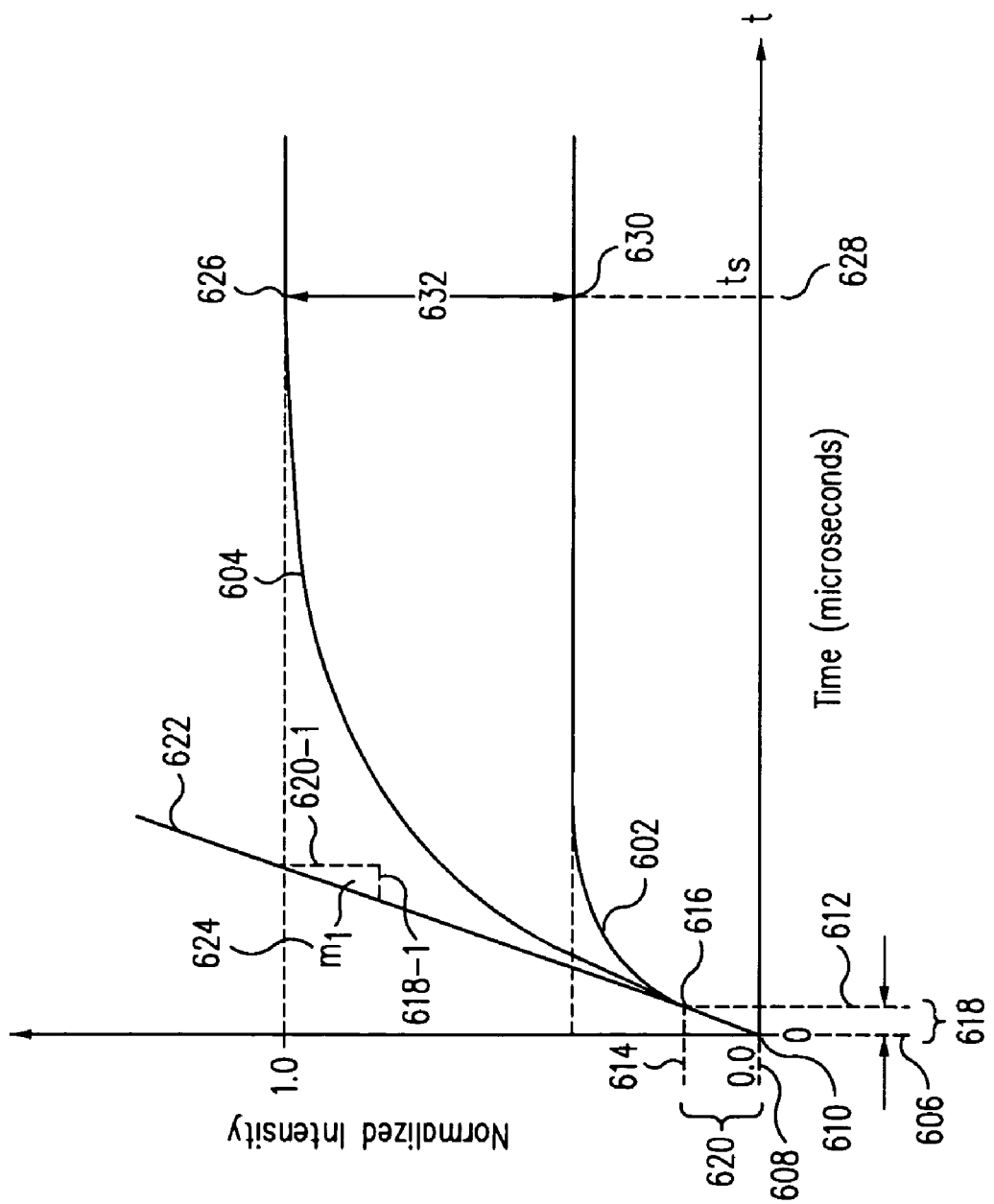
FIG. 6 shows an example scatter loss curve as compared with a predicted 0-ppm scatter loss curve where the example scatter loss curve is normalized based on the predicted 0-ppm scatter loss curve in accordance with an embodiment of the present invention.

FIG. 6 shows an example scatter loss curve 602 as compared with the predicted 0-ppm scatter loss curve 604 where the example scatter loss curve 602 is normalized based on the predicted 0-ppm scatter loss curve 604 maximum value over the measurement interval. Curve 602 corresponds to an actual cavity 104 intensity measurement over time. After light source 102 is activated, power begins to build within cavity 104, and the intensity of the detected output beam 120 begins to rise starting at first time 606 and a first intensity 608 corresponding to a first coordinate value 610 (first time, first intensity value). At a second time 612, a second intensity 614 is captured corresponding to a second coordinate value 616 (second time, second intensity value).

In this manner, a first time difference 618 corresponds to a change in time calculated by subtracting first time 606 from second time 612. Similarly, a first intensity difference 620 corresponds to a change in intensity calculated by subtracting first intensity 608 from second intensity 614. A line 622 passing through first coordinate value 610 and second coordinate value 616 has a slope 624 defined as the change in intensity 620 divided by the change in time 618. Since the shape of curve 604 is known based on the predicted or observed behavior of cavity 104, slope 624 determines the predicted unscattered saturation value 626 for curve 604 at a saturation time 628, also described as a third time 628. Similarly, the scattered saturation value 630 of curve 602 represents the actual, measured response of cavity 104 with a particular test piece 112. The difference between the unscattered saturation value 626 and the scattered saturation value 630 provides a scatter measurement 632. Unscattered intensity saturation value 626 includes absorption and transmission losses, but not scatter losses, since circulating beam 160 is completely contained within cavity 104. However, scattered intensity saturation value 630 includes absorption, transmission, and scatter losses. Subtracting the scattered intensity saturation value 630 from the unscattered intensity saturation value 626 yields the effect of scatter due to irregularities on the surface of test piece 112.

Figure 7:
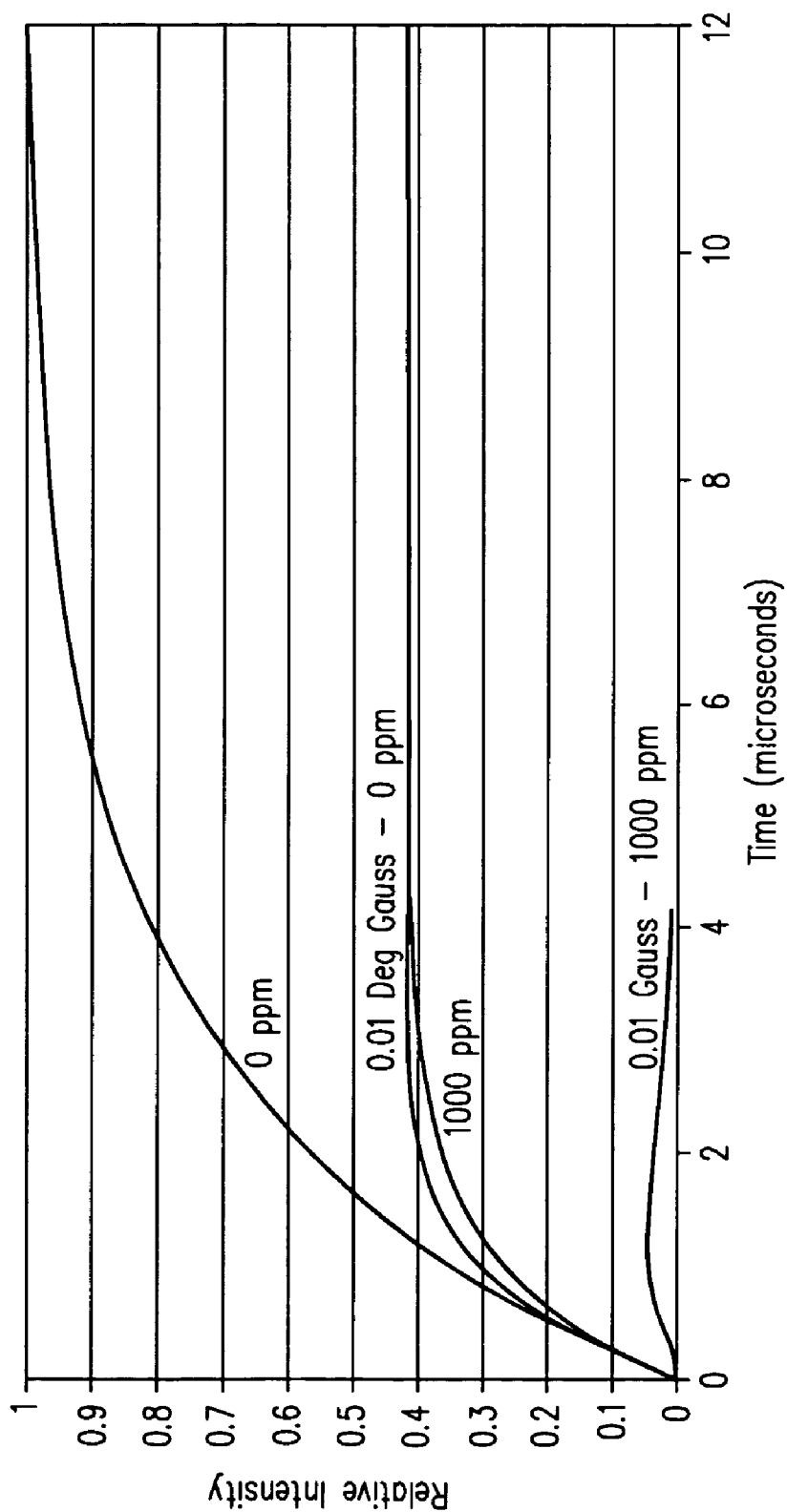
FIG. 7 shows time dependence of the intensity curves in accordance with an embodiment of the present invention.

FIG. 7 shows the time dependence of the intensity curves compared to that calculated using Equation-2. Since high performance optical coatings typically show a sharp peak in the forward scatter direction, a Gaussian scatter function is used. In this model, the scatter at the test piece surface was set to a 0.01° one sigma Gaussian function. The scatter losses in this case corresponds to about 1000-ppm. An embodiment of the present invention was validated using an optical system design and analysis tool LightTools (R) from Optical Research Associates, Pasadena, Calif. 91107. The difference between the LightTools calculation and the simple 1000-ppm decay curve is also shown in FIG. 7.

Figure 8:
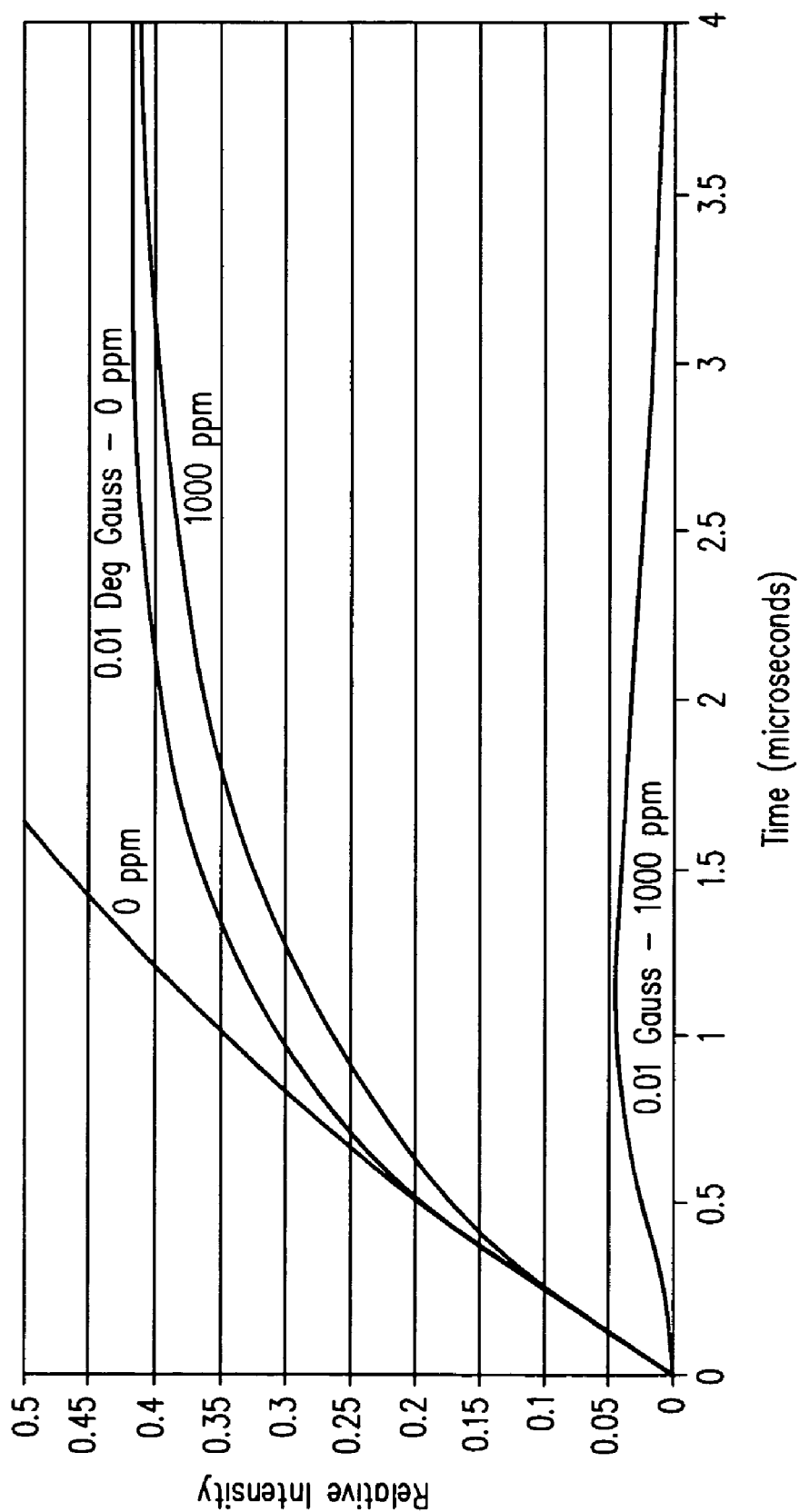
FIG. 8 shows an expanded scale of a portion of the curves shown in FIG. 7.

FIG. 8 shows an expanded scale of a portion of the curves shown in FIG. 7. Inspection of FIG. 8 reveals that the intensity rise in the Gaussian case follows the 0-ppm scatter loss curve for the first 0.5 microseconds in this example, whereas the simple decay curve diverges at 0.2 microseconds. While all of the scattered light remains confined to the cavity, it is only subjected to absorption and transmission losses. The simple 1000-ppm scatter rise curve assumes that the scatter loss starts immediately. The time dependence of the measured rise curve contains a time-based representation of the angular distribution of the forward scatter function. This may be analyzed empirically by comparing measured rise curves to numerical simulations using raytrace techniques. The angular distribution function may also be determined by using more advanced mathematical techniques, specifically those related to the statistical method known as the random walk, as described by G. H. Weiss, in an article titled Aspects and Applications of the Random Walk (1994).

Alternatively, a pulsed light source with a pulse width on the order of a few nanoseconds can be used as the light source so that the cavity decay time may be observed after the pulse is ended. Such a short pulse width may be achieved using a fast pulsed ('Q' switched) laser or other suitably pulsed or modulated light source. A chopper or shutter serves to "cut up" the light from the light source in order to provide a short duration light pulse from a continuous light output source. The decay time per circulation cycle, or round trip, in this case is simply:

$$It = [It-1] \times R \quad \text{(Equation-4)}$$

Figure 9:
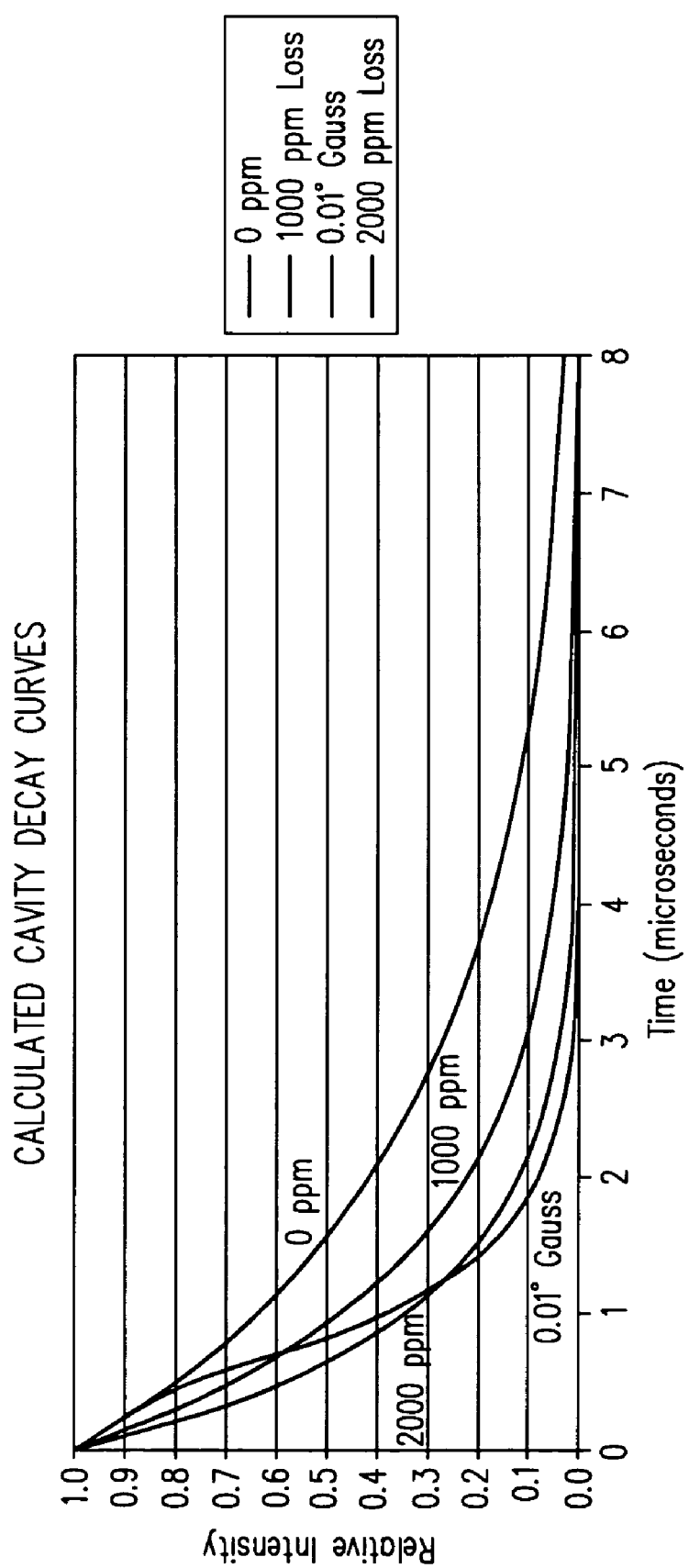
FIG. 9 shows light scatter losses can be approximated by assuming a decrease in mirror reflectivity when the size of the laser beam is much less than the mirrors so that the initial part of the decay curve contains only the transmission and absorption losses in accordance with an embodiment of the present invention.

FIG. 9 shows light scatter losses can be approximated by assuming an increase in mirror reflectivity when the size of the circulating beam cross sectional area is much less than the mirrors so that the initial part of the decay curve contains only the transmission and absorption losses. This shows the cavity decay curves for the same conditions as the rise time calculations shown in FIGS. 7 and 8. The cases of 0-ppm, 1000-ppm and 2000-pmm scatter with exponential decay and the 0.01° Gaussian scatter case are plotted. Inspection of this figure reveals that the Gaussian decay curve matches the 0-ppm scatter case for the first 0.25 microseconds then diffuses. The shape of the curve is certainly not exponential, but is closer to Gaussian. Detailed analysis, either empirical or explicit, can be used to extract the angular scatter distribution from the time dependence without undue experimentation.

Figure 10:
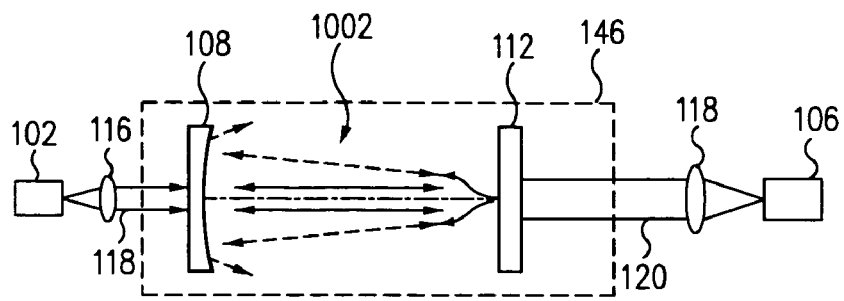
FIG. 10 shows an optical cavity apparatus where only the first end mirror and the test piece form the boundaries of cavity in accordance with an embodiment of the present invention.

FIG. 10 shows an optical cavity system 1000 where only first end mirror 108 and test piece 112 form the boundaries of a cavity 1002. Since the circulating beam contacts each optical element (108, 112) only once for each circulation cycle, the reflectivity R for the embodiment shown in FIG. 10 is $$R = R1 \times R2 \quad \text{(Equation-5)}$$

where R1 represents the reflectivity of the curved end mirror 108, and R2 represents the reflectivity of test piece 112.

Figure 11:
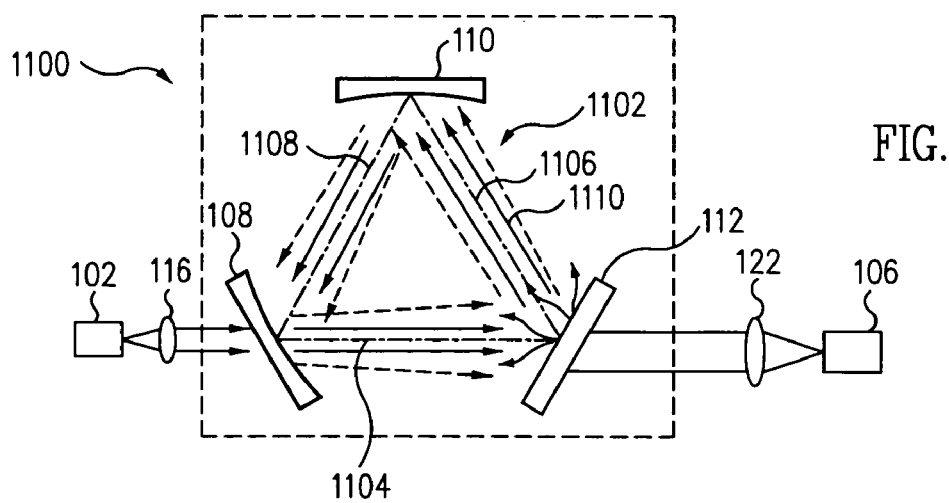
FIG. 11 shows an optical cavity apparatus including two end mirrors and a test piece arranged in a triangular shaped configuration in accordance with an embodiment of the present invention.

FIG. 11 shows an optical cavity apparatus 1100 including two end mirrors (108, 110) and test piece 112 arranged in a triangular shaped configuration where the central axis for each end mirror (108, 110) and a normal to the center of test piece 112 are all oriented towards a central point to form a cavity 1102 arranged about a triangular central axis forming an optical path within cavity 1102 for propagating the circulating beam. The central axis includes a first central axis segment 1104, a second central axis segment 1106, and a third central axis segment 1108. In this embodiment, circulating beam 1110 will contact the surface of test piece 112, second end mirror 110, and first end mirror 108 only once during each circulation cycle through the triangular ring structure. Since the circulating beam contacts each optical element (108, 110, 112) only once for each circulation cycle, the reflectivity R for the embodiment shown in FIG. 11 is $$R = R1 \times R2 \times R3 \quad \text{(Equation-6)}$$

where R1 and R3 represent the reflectivities of the curved end mirrors (108, 110), and R2 represents the reflectivity of test piece 112.

Figure 12:
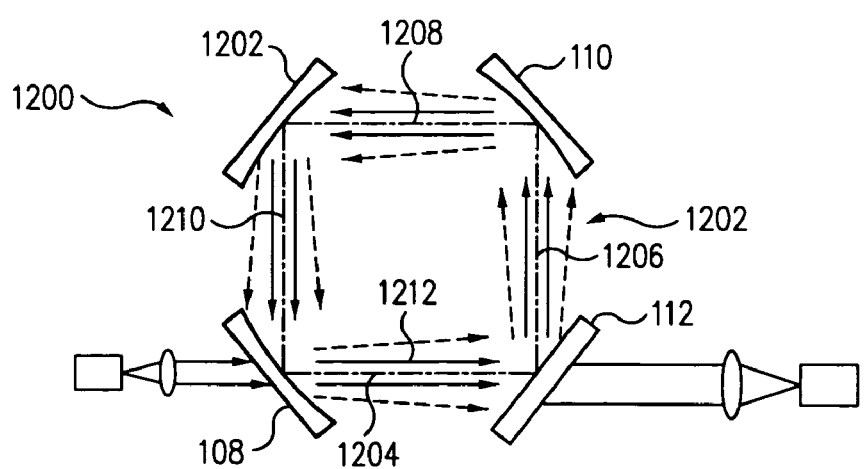
FIG. 12 shows an optical cavity apparatus including three end mirrors and a test piece arranged in a square shaped configuration in accordance with an embodiment of the present invention.

FIG. 12 shows an optical cavity apparatus 1200 including three end mirrors (108, 110, 1102) and test piece 112 arranged in a square shaped configuration where the central axis for each end mirror (108, 110, 1202) and a normal to the center of test piece 112 are all oriented towards a central point to form a cavity 1102 arranged about a square central axis or optical path path including a first central axis segment 1204, a second central axis segment 1206, and a third central axis segment 1208, and a fourth central axis segment 1210. In this embodiment, circulating beam 1212 will contact the surface of test piece 112, second end mirror 110, third end mirror 1202, and first end mirror 108 only once during each circulation cycle through the square ring structure. Since the circulating beam contacts each optical element (108, 110, 112, 1202) only once for each circulation cycle, the reflectivity R for the embodiment shown in FIG. 12 is $$R = R1 \times R2 \times R3 \times R4 \quad \text{(Equation-7)}$$

where R1, R3 and R4 represent the reflectivities of the curved end mirrors (108, 110, 1202), and R2 represents the reflectivity of test piece 112.

Figure 13:
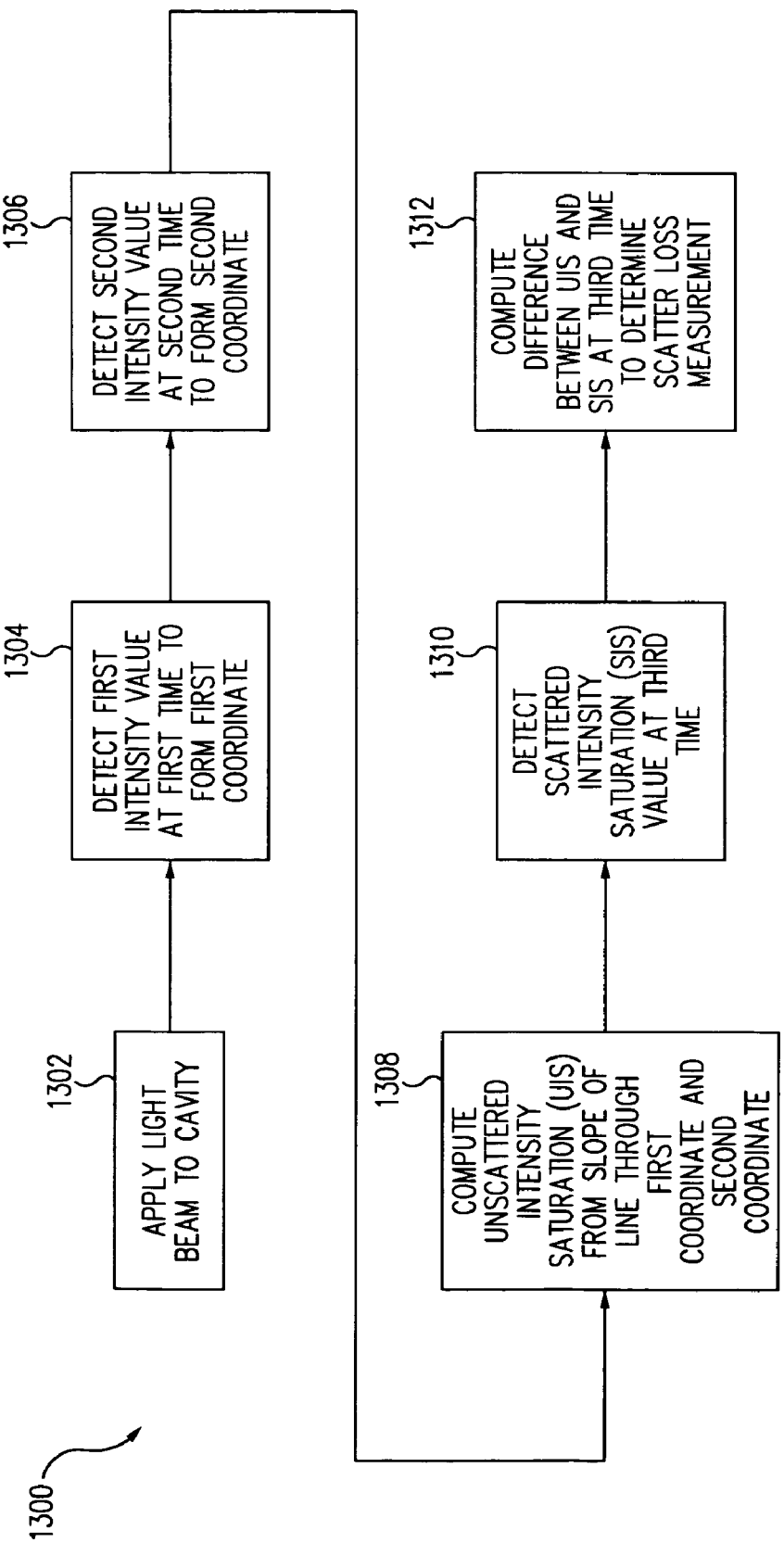
FIG. 13 shows a scatter measurement flow illustrating a series of operations in accordance with an embodiment of the present invention.

FIG. 13 shows a scatter measurement flow 1300 illustrating series of operations in accordance with an embodiment of the present invention. In reference to FIGS. 1, 6 and 13, in operation 1302, light source 102 is activated to provide an input beam for stimulating cavity 104. In operation 1304 detector 106 senses light from the output beam 120 having a first intensity value at a first time 606 in order to form a first coordinate 610 (first time, first intensity value). In operation 1306 detector 106 senses light from the output beam 120 having a second intensity value at a second time 612 in order to form a second coordinate 616 (second time, second intensity value). In operation 1308 an unscattered intensity saturation value 626 is computed based on the slope 624 of a line through first coordinate 610 and second coordinate 616. In operation 1310 a scattered intensity saturation value 630 is detected at third time 628. Finally, in operation 1312, a difference 632 is computed between the unscattered intensity saturation (SIS) value 626 and the scattered intensity saturation value (SIS) 630 as a scatter loss measurement.

Figure 14:
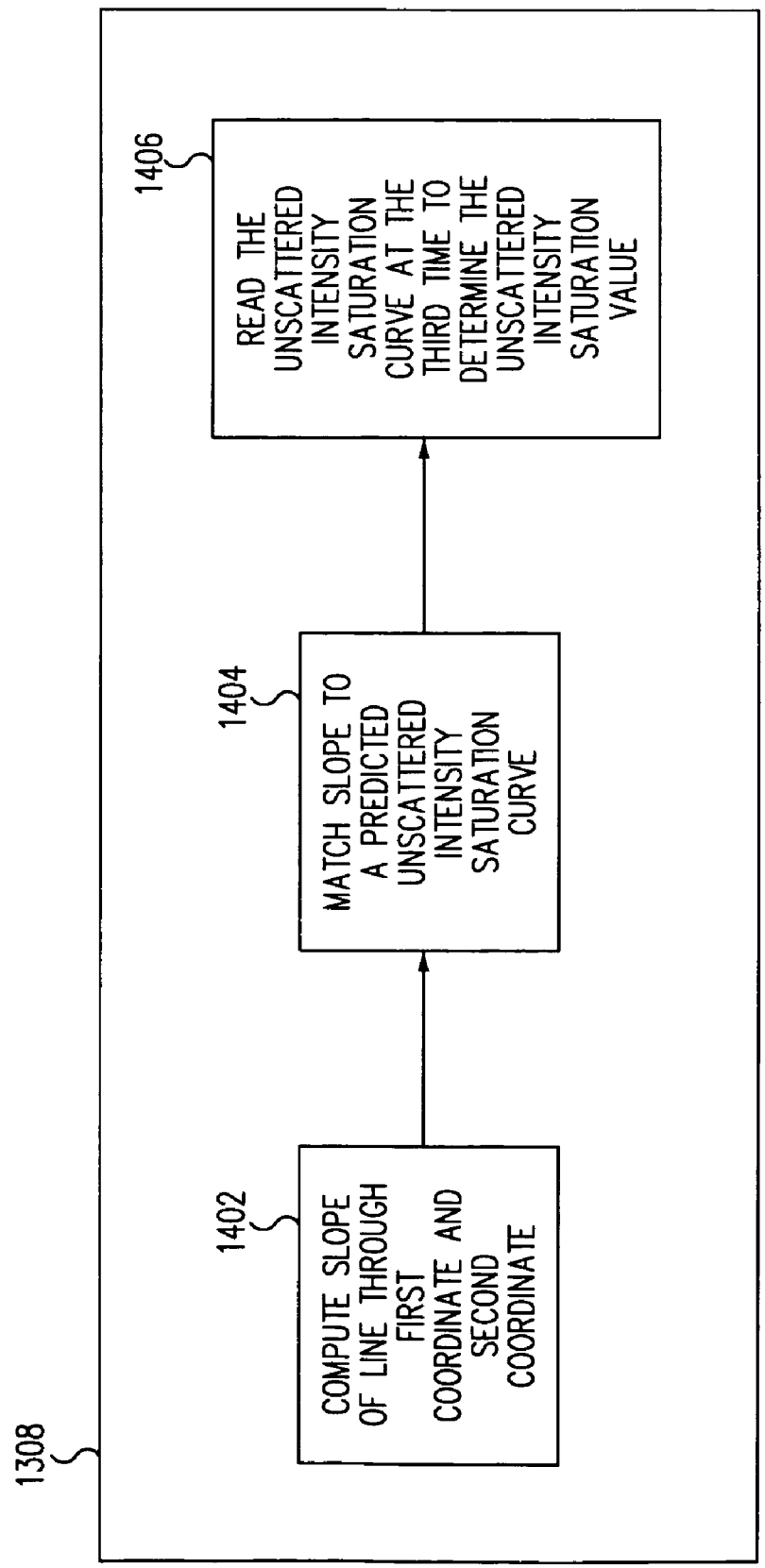
FIG. 14 shows a detailed flow for computing the unscattered intensity saturation value in accordance with an embodiment of the present invention.

FIG. 14 shows a detailed flow for operation 1308 for computing the unscattered intensity saturation value. In reference to FIGS. 6 and 14, operation 1402 computes the slope 624 of the line 622 through first coordinate 610 and second coordinate 616. Operation 1404 matches the slope 624 to a corresponding portion of a predicted unscattered intensity saturation curve 604. Operation 1406 reads the unscattered intensity saturation curve 604 at a point corresponding to third sample of scattered intensity saturation curve 602 at third time 628. In this manner, a corresponding portion of unscattered intensity saturation curve 604 is compared with a corresponding portion of scattered intensity saturation curve 602.

The embodiments described above illustrate but do not limit the invention. It should also be understood that numerous modifications and variations are possible in accordance with the principles of the present invention. Accordingly, the scope of the invention is defined only by the following claims.

I claim:

1. An apparatus for measuring light scatter loss from a test piece, the apparatus comprising:
    a light source to provide an input beam;
    an optical cavity including the test piece and at least one mirror disposed along a path, the cavity being configured to receive the input beam, to circulate a beam within the cavity as a circulating beam, and to produce an output beam, the circulating beam undergoing a progressive diffusion about the path; and
    a light detector to provide an output signal based on the intensity of the output beam, the output signal having an initial slope determining a first saturation value, the output signal having a second saturation value, wherein the initial slope is determined during a first detection period and the second saturation value is determined during a second detection time after the first detection period, and wherein the difference between the first saturation value and the second saturation value provides a scatter loss measurement.

2. The apparatus of claim 1, wherein the initial slope determines the first saturation value by matching a predicted unscattered saturation curve having the corresponding initial slope.

3. The apparatus of claim 1, wherein the test piece includes a dielectric coating.

4. The apparatus of claim 1, wherein the optical cavity includes two mirrors disposed symmetrically about the test piece, each mirror forming one leg of the optical cavity so that a circulating beam will encounter the test piece twice for each circulation cycle.

5. The apparatus of claim 1, wherein the optical cavity includes two mirrors disposed in a triangular shaped arrangement so that the circulating beam will encounter the test piece once for each circulation cycle.

6. The apparatus of claim 1, wherein the optical cavity includes three mirrors disposed in a square shaped arrangement so that the circulating beam will encounter the test piece once for each circulation cycle.

7. The apparatus of claim 1, wherein each mirror includes a concave surface.

8. The apparatus of claim 7, wherein the concave surface of each mirror is disposed toward the test piece.

9. The apparatus of claim 1, wherein the first detection period corresponds to a measurement of absorption and transmission losses, and wherein the second detection time corresponds to a measurement of scatter, absorption, and transmission losses.

10. The apparatus of claim 1, wherein the circulating beam is not completely contained within the optical cavity during the second detection time.

11. The apparatus of claim 1, wherein the circulating beam has a cross section with a predetermined diameter and the diffusion of the circulating beam results in an increase in the diameter of the circulating beam cross section within the cavity.

12. The apparatus of claim 11, wherein the mirror has a predetermined diameter, the ratio of the mirror diameter to the circulating beam cross section diameter being greater than a predetermined value corresponding to the measurement of the initial slope.

13. The apparatus of claim 12, wherein the ratio of the mirror diameter to the circulating beam cross section diameter is greater than about one-hundred to one during the first detection period.

14. The apparatus of claim 1, further comprising:
    an enclosure configured to isolate the cavity, the enclosure having a first window configured to transmit the input beam into the cavity, the enclosure having a second window configured to transmit the output beam out of the cavity.

15. The apparatus of claim 14, wherein the enclosure contains a predetermined gas.

16. The apparatus of claim 1, further comprising:
    an input lens configured to receive the input beam from the light source and produce a collimated input beam, the cavity being configured to receive the collimated input beam; and
    an output lens configured to receive the output beam from the cavity and produce a collimated output beam, the light detector being configured to receive the collimated output beam.

17. An apparatus for measuring light scatter loss from a test piece, the apparatus comprising:
    a light source to provide an input beam;
    an optical cavity including the test piece and at least one mirror disposed along a path, the cavity being configured to receive the input beam, to circulate a beam within the cavity as a circulating beam, and to produce an output beam, irregularities on the surface of the test piece resulting in a progressive diffusion of the circulating beam about the path;

a light detector to provide an output signal based on the intensity of the output beam; and a computer configured to receive a representation of the output signal and calculate an initial slope, the computer being configured to calculate a first saturation value from the initial slope, store a second saturation value, wherein the initial slope is determined during a first detection period and the second saturation value is determined during a second detection time after the first detection period, and calculate the difference between the first saturation value and the second saturation value to provide a scatter loss measurement.

18. A method of measuring light scatter loss from a test piece, the method comprising:

applying light to an optical cavity including the test piece and at least one mirror producing a circulating beam within the cavity and an output beam from the cavity;

detecting a first intensity value from the output beam at a first time to determine a first coordinate;

detecting a second intensity value from the output beam at a second time to determine a second coordinate;

detecting a scattered intensity saturation value at a third time;

computing an unscattered intensity saturation value from a predicted unscattered intensity saturation curve having a corresponding initial curve portion that matches the slope of a line through the first coordinate and the second coordinate; and computing the difference between the unscattered intensity saturation value and the scattered intensity saturation value to provide a scatter loss measurement.

19. The method of claim 18, wherein scatter within the optical cavity results in a progressive diffusion of the circulating beam.

20. The method of claim 18, wherein the period between the first time and the second time defines a first period corresponding to a measurement of absorption and transmission losses.

21. The method of claim 18, wherein the third time corresponds to a measurement of scatter, absorption, and transmission losses.

22. The method of claim 18, wherein the operation of computing an unscattered intensity saturation value from a predicted unscattered intensity saturation curve having a corresponding curve portion that matches the slope of a line through the first coordinate and the second coordinate further comprises:

computing a slope for a line between the first coordinate and the second coordinate; matching the slope to a predicted unscattered intensity saturation curve; and reading the unscattered intensity saturation curve at the third time to determine the unscattered intensity saturation value.

23. The apparatus of claim 17, wherein the initial slope determines the first saturation value by matching a predicted unscattered saturation curve having the corresponding initial slope, and wherein the first detection period corresponds to a measurement of absorption and transmission losses, and wherein the second detection time corresponds to a measurement of scatter, absorption, and transmission losses.

24. The apparatus of claim 17, wherein the circulating beam has a cross section with a predetermined diameter and the progressive diffusion of the circulating beam results in an increase in the diameter of the circulating beam cross section within the cavity.

* * * * *

UNITED STATES PATENT AND TRADEMARK OFFICE
CERTIFICATE OF CORRECTION

PATENT NO. : 7,333,206 B2 Page 1 of 1
APPLICATION NO. : 11/100780
DATED : February 19, 2008
INVENTOR(S) : Roy Clark It is certified that error appears in the above-identified patent and that said Letters Patent is hereby corrected as shown below:

On the Title Page of the patent, no. (73) Assignee: it should read:

The Boeing Company instead of --The Bowing Company--.

Signed and Sealed this

Seventeenth Day of June, 2008

JON W. DUDAS
*Director of the United States Patent and Trademark Office*